United States Patent [19]

Nelson et al.

[11] Patent Number: 4,851,461

[45] Date of Patent: * Jul. 25, 1989

[54] TETRAALKYL PIPERIDYLATED STABILIZERS FOR PLASTICS

[75] Inventors: Richard V. Nelson, Wilmington, Del.; John F. Stephen, West Chester, Pa.

[73] Assignee: ICI Americas Inc., Wilmington, Del.

[ * ] Notice: The portion of the term of this patent subsequent to Oct. 20, 2004 has been disclaimed.

[21] Appl. No.: 253,153

[22] Filed: Oct. 4, 1988

Related U.S. Application Data

[63] Continuation-in-part of Ser. No. 50,040, May 15, 1987, abandoned.

[51] Int. Cl.$^4$ .................. C08K 5/34; C07D 405/14

[52] U.S. Cl. .................. 524/98; 524/102; 524/103; 540/543; 540/597; 546/15; 546/187

[58] Field of Search .................. 524/98, 102, 103; 540/543, 597; 546/15, 187

[56] References Cited

U.S. PATENT DOCUMENTS

| | | | |
|---|---|---|---|
| 4,578,410 | 3/1986 | Takahashi et al. | 524/102 |
| 4,621,110 | 11/1986 | Battista | 524/100 |
| 4,701,485 | 10/1987 | Nelson et al. | 524/98 |
| 4,710,527 | 12/1987 | Nelson et al. | 524/98 |

*Primary Examiner*—John Kight
*Assistant Examiner*—Kriellion Morgan

[57] ABSTRACT

Acetal esters and amides possessing the polyalkyl piperidin-4-yl moiety are useful light stabilizers with synthetic polymer resins such as polyolefins and, in particular, polypropylene.

8 Claims, No Drawings

TETRAALKYL PIPERIDYLATED STABILIZERS FOR PLASTICS

This is a continuation-in-part of co-pending application Ser. No. 07/050,040, filed on May, 15, 1987 now abandoned.

The invention is directed to polymeric compositions which are resistant to degradation when exposed to actinic radiation. In particular, it is directed to resins such as polypropylene stabilized with effective amounts of cyclic acetals of aldehydes and ketones containing the polyalkylpiperidine moiety. The invention is further directed to a novel group of substances which are useful as additives for synthetic polymers which act to retard photodegradation.

Many synthetic organic polymers deteriorate rapidly when exposed to sunlight. To circumvent this rapid degradation many additives have been developed to stabilize these resins when exposed to radiation. These additives include hydroxybenzophenones, hydroxyphenylbenzotriazoles, organonickel complexes, and a number of compounds which incorporate a hindered amine, such as 2,2,6,6-tetraalkylpiperidine, which is substituted in the 4-position. However, because most of these compounds do not satisfy the stabilization requirements of polymers in their wide variety of forms and applications, there remains a need for new substances which are more effective.

Stable synthetic polymer compositions of the invention are made by their incorporation with an effective amount of the novel cyclic acetals. These acetals may be selected from those having the structures of formula I as shown in the Table of Structures wherein:

TABLE OF STRUCTURES

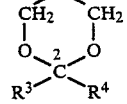  (I)

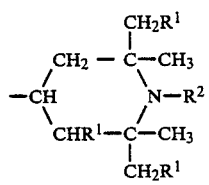  (II)

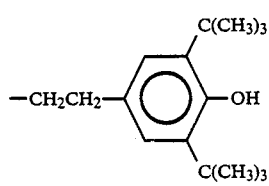  (III)

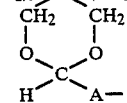  (IV)

TABLE OF STRUCTURES — continued

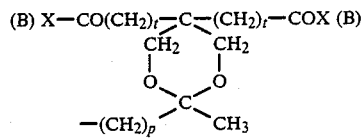  (V)

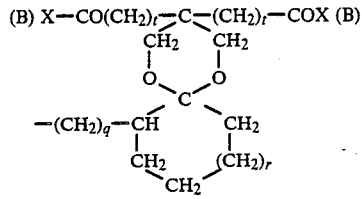  (Va)

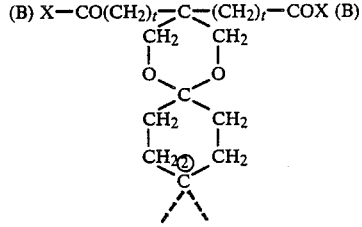  (VI)

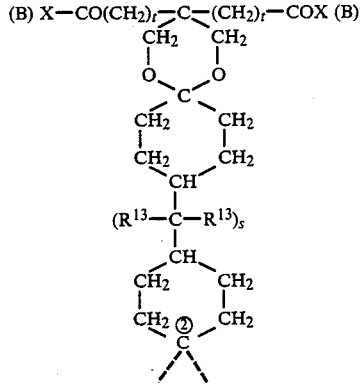  (VII)

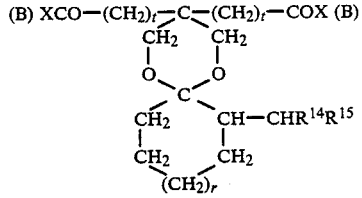  (VIII)

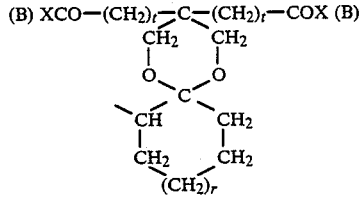  (IX)

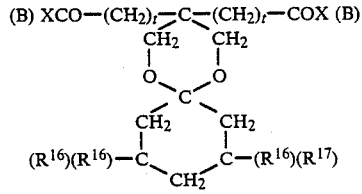  (X)

-continued
TABLE OF STRUCTURES

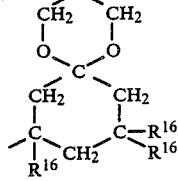 (XI)

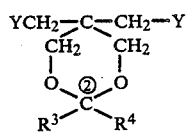 (XII)

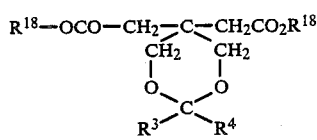 (XIII)

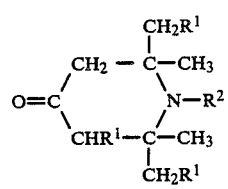 (XIV)

(B) is the group of formula II
wherein:

$R^1$ is selected from hydrogen and a alkyl group of 1-5 carbon atoms such as methyl, ethyl, n-propyl, n-butyl, n-pentyl, especially hydrogen and methyl and most preferably hydrogen;

$R^2$ is selected from hydrogen, oxyl, hydroxyl, a straight or branched chain methylene-linked alkyl group having from 1 up to 18 carbon atoms such as methyl, ethyl, octyl, octadecyl, or 2-ethylhexyl, an alkanoyl group having 2-18 carbon atoms, such as acetyl, propanoyl, butanoyl, isopentanoyl, or stearoyl, an alkenyl group of 3-4 carbon atoms, an alkenoyl group having 3-6 carbon atoms, such as acryloyl, methacryloyl, crotonyl, an alkynyl group having 3 to 6 carbon atoms such as propargyl or 2-butynyl, a cyanomethyl group, a 2,3-epoxypropyl group, an unsubstituted or substituted benzyl group of 7 to 15 carbon atoms such as 3,5-di-tert-butyl-4-hydroxybenzyl, 3-tert-butyl-4-hydroxybenzyl or 3-tert-butyl-4-hydroxy-5-methylbenzyl, a group —$CH_2CH(OR^5)$—$R^6$ and a group of the formula

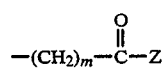

wherein Z is a group selected from —$OR^7$ and —$N(R^8)(R^9)$ when m is 1 or 0 and when m is 0, Z can be a group —$C(O)$—$OR^{10}$, $R^5$ is selected from hydrogen, an aliphatic group of 1-18 carbon atoms such as those of $R^2$, an araliphatic group such as benzyl and phenethyl, and a aliphatic acyl group having 2-18 carbon atoms such as those of $R^2$, $R^6$ is selected from hydrogen, an alkyl group of 1-16 carbon atoms and phenyl, $R^7$ is selected from an alkyl group of 1-18 carbon atoms, a cycloalkyl of 5-12 carbon atoms such as cyclopentyl, cyclohexyl, cyclooctyl, cyclododecyl, allyl, benzyl, phenyl, and a group of formula II wherein $R^1$ and $R^2$ are as described above, and $R^8$ and $R^9$, same or different, are selected from hydrogen, an alkyl group having 1-8 carbon atoms such as methyl, ethyl, hexyl, a cycloalkyl group having 5-12 carbon atoms such as those of $R^7$, aryl groups having 6-10 carbon atoms such 4-methylphenyl, 2-methylphenyl, 4-butylphenyl, and aralkyl groups having 7-15 carbon atoms such as benzyl, o, m, p, alkyl substituted benzyl, and phenethyl. In addition, $R^8$ and $R^9$ together with the nitrogen atom to which they are attached can form a 5-7 membered ring such as pyrrolidine, piperidine and homopiperidine, and $R^{10}$ is selected from $C_{1-18}$ alkyl such as those of $R^2$, phenyl or benzyl, and is preferably $C_{1-2}$ alkyl.

(X) in formula I is either —O— or —$NR^{11}$— where $R^{11}$ is selected from hydrogen or an alkyl group of 1-8 carbon atoms such as methyl, ethyl, butyl, or octyl.

(t) is 0 or 1.

$R^3$ and $R^4$ may independently be selected from hydrogen, an alkyl group of 1 to 14 carbon atoms such as methyl, ethyl, n-propyl, isopropyl, isooctyl, 3-heptyl, an alkenyl group of 2 to 4 carbon atoms, aryl, aralkyl, a group —$(CH_2)_nCO$—$OR^{12}$ where n is 0 or 1, and a group of formula III. $R^{12}$ is selected from a straight or branched chain alkyl group of up to 18 carbon atoms in length or a group of formula II.

When $R^3$ is hydrogen, $R^4$ is a group of formula IV where A is a 1 to 10 carbon alkylene group, a phenylene group or a direct bond.

When $R^3$ is methyl $R^4$ is a group of formula V where p is 1-10, when $R^3$ is ethyl $R^4$ is a group of formula V where p is 1-9. When $R^3$ is either hydrogen or methyl, $R^4$ is a group of formula Va where q is 1 to 3 and r is 1 to 7.

$R^3$ and $R^4$ together with the carbon atoms to which they are attached can form a cycloalkyl group having 5-12 carbon atoms such as cyclopentyl, cyclohexyl, cyclooctyl, cyclododecyl or denote a group of the formula VI or the group of formula VII where the carbon atom labelled 2 is the same as that labelled 2 in formula I wherein in formula VII, s is either 0 or 1. Where s is 1 then $R^{13}$ is lower alkyl such as methyl or ethyl, and when q is 0 the rings are connected by a direct bond. $R^3$ and $R^4$ may be connected to form a cycloalkyl group as shown in formula VIII wherein r is 1 to 7, $R^{14}$ is hydrogen or an alkyl group of 1-11 carbon atoms and $R^{15}$ is the group of formula IX. $R^3$ and $R^4$ may also form a cyclohexyl group as shown in formula X which has been substituted in the 3 and 5 positions, where $R^{16}$ is hydrogen or methyl and $R^{17}$ is the group of formula XI.

The acetals of formula I can be prepared from the corresponding aldehyde or ketone by reacting them with a diol of the formula $(HOCH_2)_2C(CH_2Y)_2$ or $(HOCH_2)_2C(CO_2R)_2$ where R is an alkyl group having 1-18 carbon atoms using a suitable acid catalyst and a suitable solvent as generally known in the art for the preparation of acetals. The aldehyde or ketone starting material is generally available commercially. In cases where the starting aldehyde or ketone is not available commercially they can be prepared easily according to a variety of known literature procedures.

The group Y may be any halogen which can serve as a leaving group such as Cl, Br or I but it is preferred that Y be Cl or Br. The preferred diols can be prepared by the chlorination or bromination of pentaerythritol as described in U.S. Pat. Nos. 3,607,953 and 3,932,541.

Examples of suitable acid catalysts are numerous, however, without introducing any limitations are mentioned p-toluenesulfonic acid and methanesulfonic acid. Examples of suitable solvents are cyclohexane and benzene.

The acetal resulting from reaction of the dihaloneopentyl glycol and the appropriate aldehyde or ketone is generally isolated by solvent extraction and after concentration can be purified by either distillation or crystallization.

Several of the dihalo acetals serving as precursors for the compounds of this invention have been reported previously. In particular these compounds may be found in Zh. Obshch. Khim, 1981, 51 (4), 934–40, Zh. Org. Khim 1985, 21 (1), 131–5 and 1981, 17 (7), 1536–9, Bull, Soc. Chim. Belg., 85 (9), 681–96 and 673–79, and Zh. Prikl, Khim. (Leningrad), 50 (1), 212–14.

The resultant dihaloacetals of formula XII can then be tranformed into the compounds of the invention via the sequence: cyanation, hydrolysis and/or esterification and finally, transesterification.

In general the cyanation is performed in a dipolar aprotic solvent such as dimethylsulfoxide, dimethyl formamide, N-methylpyrrolidone, etc., using a cyanide salt such as sodium cyanide or potassium cyanide. The reaction can be carried out at a temperature ranging from 20° C. to 160° C. but it is preferred that the reaction be run at about 100°–130° C. The resulting dinitrile can be isolated by solvent extraction and purified by either distillation or crystallization.

The dinitriles are then transformed into the corresponding diesters of formula XIII where $R^{18}$ is a lower alkyl such as methyl, ethyl, etc., via a single step or two step process. In the case where a single step is used the dinitrile is treated with anhydrous hydrogen chloride in the desired alcohol solvent such as methanol or ethanol. The imidate hydrochloride which forms can then be converted to yield the desired diester. This reaction is commonly known as the Pinner reaction.

The alternative route which may be used is the hydrolysis of the dinitrile, generally under alkaline conditions such as aqueous potassium hydroxide to yield the correspondiang dicarboxylate salt. A cosolvent can be used to help the hydrolysis if necessary, such as an alcohol or a dipolar aprotic solvent. Optionally the hydrolysis can be accelerated by catalysis with hydrogen peroxide.

The resultant salt can be esterified using an alkyl halide or dialkyl sulfate. In general these materials are chosen from methyl chloride, methyl iodide, dimethyl sulfate, diethyl sulfate, etc. Optionally, the salt can be converted to the diacid by neutralization and then converted to the dimethyl ester using diazomethane.

The resulting dialkyl esters are then transformed into the corresponding piperidine compounds of the invention in either a single step or, in the cases where $R^2$ is other than hydrogen or alkyl, an additional step is generally used. The transesterification or amidation reaction can be performed either neat or in a suitable solvent using basic catalysts as commonly used in the art. Examples of suitable catalysts without introducing any limitations are lithium amide and sodium methoxide. Examples of suitable solvents are ligroine and toluene.

The 4-hydroxypolyalkylpiperidines are the 4-aminopolyalkylpiperidines used to convert the acetals into the compounds of the invention are known from German Pat. No. 2,352,658 and U.S. Pat. No. 3,684,765. In general, the 4-hydroxy compounds are prepared from the corresponding 4-oxopiperidines by reduction via catalytic hydrogenation over Raney Nickel and the 4-amino compounds are synthesized via a reductive amination using ammonia or the particular primary amine of interest.

The 4-oxopiperidines of formula XIV can be prepared by reaction of ammonia with an aliphatic ketone. The reaction of ammonia with acetone to yield triacetoneamine is well-known and various processes exist in the art for its manufacture. The reaction of ammonia with methyl ethyl ketone had been described by W. Traube in Chem. Ber. 41, 777 (1908).

Compounds of the formula XIV which carry other alkyl substituents in the 2-position and the 6-position can be prepared in a two step process following the procedures outlined in Helv. Chem. Acta 30, 1114 (1947) and Monatsh. Chem. 88, 464 (1957), followed by hydrolysis of the resulting pyrimidine.

The introduction of an alkyl, alkenyl, alkynyl, aralkyl and 2,3-epoxypropyl group can be achieved by reaction of the initially prepared ester or amide containing the free N—H of the polysubstituted piperidine with suitable halides like methyl iodide, ethyl bromide, propyl bromide, dodecyl chloride, and octadecyl chloride, allyl bromide, methallyl chloride, butenyl chloride, propargyl bromide, benzyl chloride, phenethyl bromide, and epichlorohydrin. The generated hydrogen halide can be scavenged by the addition of an inorganic base such as carbonate or hydroxide or by the addition of an organic amine such as triethylamine to the reaction mixture.

An alternative way of preparing the compounds of the invention which contain a 1-alkyl, 1-alkenyl, 1-alkynyl, 1-aralkyl, or 2,3-epoxypropyl group, especially when the desired invention compound is an ester, is to prepare the 1-substituted polyalkylpiperidin-4-ol as described in U.S. Pat. No. 4,014,887 and perform the transesterification in the manner as stated previously.

The introduction of an alkanoyl or an alkenoyl group can be performed by acylation of the parent N—H compound of formula I (wherein $R^2$ is H) using the suitable acid halide or, when convenient, the acid anhydride. If the acid halide is used the generated hydrogen can be scavenged in the same manner as stated previously. Examples of such groups are acetyl chloride, propionyl chloride, hexanoyl chloride, dodecanoyl chloride, octadecanoyl chloride, acetic anhydride, and propionic anhydride.

For the compounds when $R^2$ is the group —CH$_2$CH(OR$^5$)—R$^6$ the substituent can be introduced by reaction of the parent N—H compound of formula I (where $R^2$ is H) with the corresponding alkylene oxide such as ethylene oxide, propylene oxide and styrene oxide. The resulting hydroxy compound can be acylated in the manner commonly known in the art using the suitable acid halide and can be alkylated by generating the alkoxide using a base like sodium hydride and treating it with the desired alkyl or aralkyl halide.

When $R^2$ is the group $-(CH_2)_m COZ$ and m is zero the appropriate group can be attached by reacting the parent N—H compound of formula I (where $R^2$ is H) with a chloroformate such as methyl chloroformate, ethyl chloroformate, allyl chloroformate, hexyl chloroformate, decyl chloroformate, octadecyl chloroformate, and phenyl chloroformate. The preparation of the oxamide half esters can be achieved by reaction of the parent N—H compound with the oxalyl chloride monoalkylester such as oxalyl chloride monomethylester and oxalyl chloride monoethylester and scavenging the generated hydrogen chloride with a base as stated previously.

For preparation of the corresponding ureas the parent N—H the compound of formula I (where $R^2$ is H) can be treated withe the suitable carbamyl halide such as methyl carbamyl chloride, ethyl carbamyl chloride, butyl carbamyl chloride, phenyl carbamyl chloride, dimethyl carbamyl chloride, diethylcarbamyl chloride, dihexylcarbamyl chloride, pyrrolidine carbamyl chloride, piperidine carbamyl chloride, and homopiperidine carbamyl chloride. Alternatively, the ureas can be prepared by treating the parent N—H compound with the suitable isocyanate.

Compounds of formula I wherein $R^2$ is the oxyl radical are obtainable from the corresponding N—H compounds of formula I (where $R^2$ is H) by oxidation with the peroxide such as hydrogen peroxide in the presence of a catalyst like sodium tungstate or with percarboxylic acids like metachloroperoxybenzoic acid.

When $R^2$ is the group —$(CH_2)_m$—COZ and m is 1 the appropriate group can be attached by reacting the parent N—H compound of formula I (where $R^2$ is H) with an ester of chloroacetic acid such as methyl chloroacetate, ethyl chloroacetate, cyclohexylchloroacetate, benzyl chloroacetate, allyl chloroacetate and phenyl chloroacetate.

The compounds of this invention are effective light stabilizers for synthetic organic polymers.

The following examples are offered to demonstrate but not limit the scope of the invention. Each compound has been characterized by NMR and MS spectroscopy.

EXAMPLE 1

1,5-Dioxaspirol[5.5]undecane-3,3-diacetic acid, diester with 2,2,6,6-tetramethylpiperidin-4-ol

Preparation A 1,5-dioxaspiro[5.5]undecane-3,3-bis(bromomethyl)

A mixture of cyclohexanone (7.17 g, 73 mmol) and dibromoneopentylglycol (10.14 g, 73 mmol) in 100 ml of cyclohexane was heated to reflux. The paratoluenesulfonic acid catalyst (0.70 g, 3.65 mmol) was added and the produced water was removed via a Dean-Stark trap. After about 2 hr the mixture was removed from the heat, cooled to ambient temperature and partitioned with water after destroying the catalyst with aqueous sodium hydroxide. The organic solution was dried ($Na_2SO_4$) and concentrated to yield the product as a viscous liquid (24.77 g, 95% purity). This material was used as obtained for the next reaction.

Preparation B 1,5-Dioxaspiro[5.5]undecane-3,3-bis(cyanomethyl)

To a mixture of the ground potassium cyanide (5.56 g, 85.3 mmol) in 90 ml of dimethylsulfoxide was added 10 ml solution of the product of Preparation A (0.30 g, 21.3 mmol). The mixture was heated to 120°–130° C. for 4 hr after which time it was cooled to room temperature, poured into about 200 ml of water and extracted with ethyl acetate (3×100 ml). The organic solution was back-washed with water, dried ($Na_2SO_4$) and concentrated to yield the crude dinitrile as a dark viscous liquid. The material was purified via bulb-to-bulb distillation to yield 3.80 g (76% yield, 99% purity by GC, bp 130° C. @ 0.1 mm) of the product as a very light yellow liquid which solidified upon standing.

Preparation C 1,5-Dioxaspirol[5.5]undecane-3,3-diacetic acid

To a mixture of the dinitrile of Preparation B (3.80 g, 16.21 mmol) in 20 ml of aqueous potassium hydroxide (7.27 g, 129 mmol) was added 5 ml of 30% hydrogen peroxide. The mixture was heated at reflux for 6 hr after which it was cooled to room temperature, extracted with diethyl ether (50 ml), acidified with 10% aqueous HCl to about pH 3. The solution was extracted with etyl acetate (3×75 ml), dried ($Na_2SO_4$) and concentrated to yield the diacid as a light yellow solid (4.0 g, 80%).

Preparation D 1,5-Dioxaspirol[5.5]undecane-3,3-diacetic acid, dimethyl ester A solution of the diacid of Preparation C (2.72 g, 10 mmol) in 20 ml of diethyl ether was added dropwise to an ethereal solution of diazomethane (about 1.26 g, 30 mmol) at 0°–5° C. Upon completion of the addition the mixture was permitted to stand for 15 minutes before the excess diazomethane was destroyed with acetic acid. The solution was concentrated to yield the product as a light yellow viscous liquid (3.2 g). This substance was purified by bulb-to-bulb distillation to yield 2.83 g (94% purity, bp 140°–150° C. @ 0.1 mm) of an almost colorless liquid.

To the product of Preparation D (2.29 g, 94%, 7.26 mmol) and 2,2,6,6-tetramethylpiperidin-4-ol (2.29 g, 14.56 mmol) in 50 ml of ligroine (90°–110° C.) at reflux was added the lithium amide catalyst (23 mg, 1 mmol). The produced alcohol was removed by intermittent draining of the Dean-Stark trap. After 4 hrs the reaction was complete. The mixture was cooled, the catalyst was destroyed by the addition of acetic acid (60 mg, 1 mmol) and the mixture was partitioned between ligroine and water. After drying ($Na_2SO_4$) and concentration the product was obtained as a viscous very light yellow liquid which solidified upon trituration with petroleum ether (35°–60° C.) to yield a white solid (3.6 g, 90%) having a melting point of 108°–109° C.

EXAMPLE 2

1,5-Dioxaspiro[5.5]undecane-3,3-diacetic acid, diester with 1,2,2,6,6-pentamethylpiperidin-4-ol To the product of Preparation D (0.26 g, 0.86 mmol) and 1,2,2,6,6-pentamethylpiperidin-4-ol (0.30 g, 1.77 mmol) in 20 ml of ligroine (90°–110° C.) at reflux was added the lithium amide catalyst (12 mg, 0.5 mmol). The mixture was permitted to stir at reflux for about 2 hr with gradual removal of the solvent. After this time the mixture was cooled, the catalyst destroyed and the mixture partitioned between ligroine water. Drying ($Na_2SO_4$) and concentration yielded the product as a white solid (0.48 g, 95%) having a melting point of 71°–74° C.

EXAMPLE 3

1,5-Dioxaspiro[5.5]undecane-3,3-diacetic acid, diamide with 4-amido-2,2,6,6-tetramethylpiperidine To a mixture of (3.00 parts) of the compound of Preparation D and (3.43 parts) of 4-amino-2,2,6,6-tetramethylpiperidine in 30 ml of dimethyl sulfoxide was added sodium hydride (0.5 parts). The mixture was heated to 100°-120° C. for 36 hours after which it was partitioned between ethyl acetate and water upon cooling. The organic solution was dried ($Na_2SO_4$) and concentrated. After subsequent purification the product was characterized by NMR and mass spectroscopy.

The acetals derivatives of the invention are particularly useful as light stabilizers for synthetic polymers which undergo degradation in the presence of air and actinic radiation. As used herein polymers are intended to embrace polyolefins including homopolymers of olefins such as low density and high density polyethylene, propropylene, polystyrene, polybutadiene, polyisoprene and the like; and copolymers of olefins with other ethylenically unsaturated monomers such as ethylene-propylene copolymer, ethylene-butylene copolymer, ethylene-vinyl acetate copolymer, styrene-butadiene copolymer, acrylonitrile styrene-butadiene copolymer and the like; polyvinyl chlorides and polyvinylidene chlorides including homopolymers of each of vinylchloride and vinylidene chloride, vinylchloride-vinylidene copolymers and copolymers of each vinylchloride and vinylidene chloride with vinyl acetate or other ethylenically unsaturated monomer; polyacetal as such polyoxymethylene and polyoxyethylene; polyesters such as polyethyleneterephthalate; polyamide such as 6-nylon, 6,6,-nylon and 6,10-nylon and polyurethanes and polymers derived from $\alpha,\beta$-unsaturated acids and derivatives thereof, polyacrylates and polymethacrylates, polyacrylic amides and polyacrylonitrile, as well as copolymers of acrylic acid and one or more of its derivatives with a melamineformaldehyde resin.

Synthetic polymers have been widely utilized in the art in view of their excellent properties in various forms or shapes, for example, filaments, fibers, yarns, filament sheet, other molded articles made from latex foam. However, these polymers have some drawbacks such as poor light and heat stabilities among others. Stated illustratively, polyolefins and polyurethane elastomers frequently tend to undergo severe deterioration when exposed to light such as sunlight or ultraviolet light and polyvinyl chloride and polyvinylidene chlorides frequently tend to deteriorate and become colored by the action of light and heat together with elimination of hydrogen chloride. Polyamides are also frequently subjected to photodegradation. For the purpose of stabilizing these synthetic polymers against such degradation, there have been proposed in the art a number of stabilizers. For example, in the case of polyolefins, benzotriazole and benzophenone compounds; for polyurethanes, phenol compounds and benzophenone compounds; and for polyvinylchlorides and vinylidene chlorides, lead salts such as basic lead silicate and trisilicate, lead maleate and organic tin compounds such as dibutylinlaurate and dibutyltinmaleate.

The resin should have incorporated within the effective stabilizing amount of a compound described by formula I. The amount will depend upon the nature of the plastic and the amount of radiation to which the plastic will be subject. Generally an amount between about 0.01% and 5.0% by weight of the polymer is effective. Preferably they may be used in concentrations between 0.05 and 1% by weight.

In addition, the light stabilizers of formula I may be used with fillers and additional stabilizers including antioxidants, flame retardant stabilizers, anti-slipping and antistatic agents, supplemental light stabilizers, pigments, dyes, lubricants, etc.

Suitable antioxidants include those of the hindered phenol type such as 2,6-di-t-butyl-p-cresol; 4,4'-bis(2,6-di-t-butylphenol); 4,4'-bis(2,6-diisopropylphenol); 2,4,6-tri-t-butylphenol; 2,2'-thiobis(4-methyl-6-t-butylphenol); octadecyl-3-(3',5'di-t-butyl-4'-hydroxyphenyl)-propionate; pentaerythrityl tetrakis(3,5-di-t-butyl-4-hydroxyphenyl)propionate; 1,3,5-tris(3',5'-di-t-butyl-4-hydroxybenzyl)isocyanurate; 1,3,5-tris((3,5'-di-butyl-4'-hydroxyphenyl)proprionate)isocyanurate; 1,3,5-tris(3,5-di-t-butyl-4-hydroxybenzyl)-2,4,6-dimethylbenzyl)-s-triazine-2,4,6-(1H,3H,5H)-trione and esters of thiodipropionic acid such as dilaurylthiodipropionate and distearylthiodipropionate etc.; hydrocarbyl phosphites such as triphenyl phosphite, trinonyl phosphite, diodecyl pentaerythritol diphosphite, diphenyldecyl phosphite, tris-(2,4-di-t-butylphenyl)phosphite, bis(2,4-di-t-butylphenyl)pentaerythritol diphosphite, etc, in combinations thereof.

Suitable supplemental light stabilizers include those of the benzotriazole class, such as 2-(2'-hydroxy-5'-t-octylphenyl)benzotriazole; 2(2'-hydroxy-3',5'-di-t-butyl-phenyl)-5-chlorobenzotriazole; 2-2'-hydroxy-5'-methylphenyl)benzotriazole; 2-(2'-hydroxy-3'-t-butyl-5'-methylphenyl)-5-chlorobenzotriazole; 2-(2'-hydroxy-5'-t-butylphenyl)benzotriazole; 2-(2'-hydroxy-3',5'-di-t-amylphenyl)benzotriazole; those of the hydroxybenzophenone type such as 2-hydroxy-4-methoxybenzophenone; 2-hydroxy-4-octyloxybenzophenone; 2,2'-dihydroxy-4,4'-di-methoxybenzophenone; hindered phenol esters, such as n-hexadecyl 3,5-di-t-butyl-4-hydroxybenzoate, and 2',4'-di-t-butylphenol-3,5-di-t-butyl-4-hydroxybenzoate; metal complexes such as nickel complexes of 2,2'-thiobis(4,6-octyl-phenyl), nickel butylamine complexes of 2,2'-thiobis(4-t-octylphenol); nickel complexes of bis(4-t-octyl-phenol)sulphone; nickel dibutyl thiocarbamate; nickel salts of 4-hydroxy-3,5-di-t-butylbenzylphosphonic acid monoalkyl esters where alkyl is methyl, ethyl, propyl, butyl, etc.; nickel complexes of to 2-hydroxy-4-methylphenyl undecylketoneoxime. Further illustrative examples of suitable antioxidants of supplemental light stabilizers can be found in columns 3 and 4 of U.S. Pat. Nos. 3,488,290 and 3,496,134.

EXAMPLE 4-5

In order to further illustate the effectiveness of the above-described compounds as light stabilizers the previously described material of Examples 1 incorporated into a commercially available polypropylene resin manufactured by Hercules Corporation as PRO-FAX[3] 6301 Polypropylene Resin. The light stabilizer was incorporated with the polypropylene by solvent blending (methylene chloride) at concentrations of 0.25% by weight of the total resin composition and as a primary antioxidant stearyl beta-3,5-di-t-butyl-4-hydroxyphenylpropionate was used at the concentration of 0.2%. The resin was the extruded at 200° C. and compression molded at 6,000 psi at 188° C. to produce films having thickness of 5 mils. Each test film and a control film produced in the same manner was exposed to Xenon Arc in an Atlas Weather-o-meter until the infrared carbonyl absorption increased by 0.5, which is considered to be the failure point.

TABLE 1

| Example No. | Stabilizer | Hours to Failure |
|---|---|---|
| 4 | Control | 420 |
| 5 | Product of Example 1 | 3080 |

What is claimed is:

1. A compound of the formula I wherein
(B) is the group of formula II wherein:
$R^1$ is selected from the group consisting of hydrogen and an alkyl group of 1-5 carbon atoms;
$R^2$ is selected from the group consisting of hydrogen, oxyl, hydroxyl, a straight or branched chain methylene-linked alkyl group having from 1 up to 18 carbon atoms, an alkanoyl group having 2-18 carbon atoms, an alkenyl group of 3-4 carbon atoms, an alkenoyl group having 3-6 carbon atoms, an alkynyl group having 3 to 6 carbon atoms, a cyanomethyl group, a 2,3-epoxypropyl group, a benzyl group of 7 to 15 carbon atoms, a group —$CH_2CH(OR^5)$—$R^6$ and a group of the formula:

wherein Z is a group selected from —$OR^7$ and —$N(R^8)(R^9)$ when m is 1 or 0 and when m is 0, Z can be a group —C(O)—$OR^{10}$;
$R^5$ is selected from the group consisting of hydrogen, an aliphatic group of 1-18 carbon atoms such as those of $R^2$, an araliphatic group and an aliphatic acyl group having 2-18 carbon atoms such as those of $R^2$;
$R^6$ is selected from the group consisting of hydrogen, an alkyl group of 1-16 carbon atoms and phenyl;
$R^7$ is selected from the group consisting of an alkyl group of 1-18 carbon atoms, a cycloalkyl of 5-12 carbon atoms and a group of formula II wherein $R^1$ and $R^2$ are as described above; and
$R^8$ and $R^9$, same or different, are selected from the group consisting of hydrogen, an alkyl group having 1-8 carbon atoms, a cycloalkyl group having 5-12 carbon atoms such as those of $R^7$, aryl groups having 6-10 carbon atoms and aralkyl groups having 7-15 carbon atoms; $R^8$ and $R^9$ together with the nitrogen atom to which they are attached can form a 5-7 membered ring such as pyrrolidine, piperidine and homopiperidine; and
$R^{10}$ is selected from the group consisting of alkyl groups having 1-18 carbon atoms such as those of $R^2$, phenyl or benzyl;
(X) in formula I is either —O— or —$NR^{11}$— where $R^{11}$ is selected from hydrogen or an alkyl group of 1-8 carbon atoms;
(t) is 0 or 1;
$R^3$ and $R^4$ may independently be selected from the group consisting of hydrogen, an alkyl group of 1 to 14 carbon atoms, an alkenyl group of 2 to 4 carbon atoms, aryl, aralkyl, a group —$(CH_2)_n$CO—$OR^{12}$ where n is 0 or 1, and a group of formula III, $R^{12}$ is selected from an alkyl group of up to 18 carbon atoms or a group of formula II; when $R^3$ is hydrogen, $R^4$ is a group of formula IV where A is a 1 to 10 carbon alkylene group, a phenylene group or a direct bond; when $R^3$ is methyl, $R^4$ is a group of formula V where p is 1-10, and when $R^3$ is ethyl, $R^4$ is a group of formula V where p is 1-9;
when $R^3$ is either hydrogen or methyl, $R^4$ is a group of formula Va where q is 1 to 3 and r is 1 to 7; $R^3$ and $R^4$ together with the carbon atoms to which they are attached may form a cycloalkyl group having 5-12 carbon atoms or denote a group of the formula VI or the group of formula VII where the carbon atom labelled 2 is the same as that labelled 2 in formula I wherein in formula VII, s is either 0 or 1, where if s is 1 then $R^{13}$ is lower alkyl of up to 2 carbon atoms and when q is 0 the rings are connected by a direct bond; $R^3$ and $R^4$ may be connected to form a cycloalkyl group as shown formula VIII wherein r is 1 to 7, $R^{14}$ is hydrogen or an alkyl group of 1-11 carbon atoms and $R^{15}$ is the group of formula IX; $R^3$ and $R^4$ may be a cyclohexyl group as shown in formula X which has been substituted in the 3 and 5 positions, where $R^{16}$ is hydrogen or methyl and $R^{17}$ is the group of formula XI, and wherein said formulas are as follows:

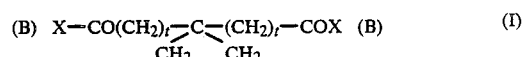
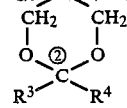

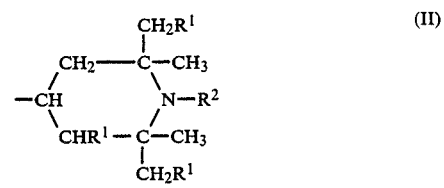

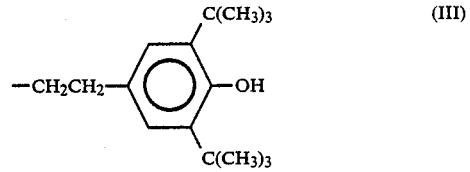

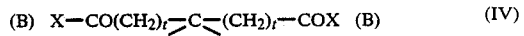
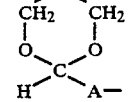

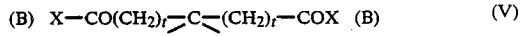
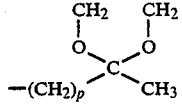

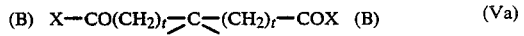
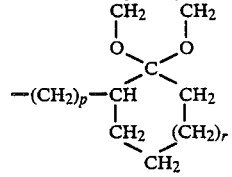

-continued

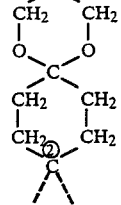 (VI)

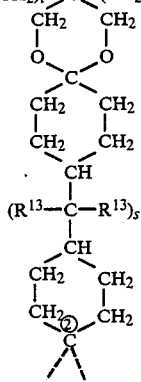 (VII)

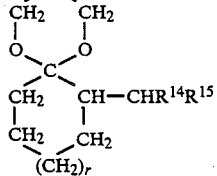 (VIII)

-continued

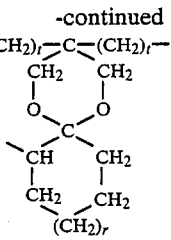 (IX)

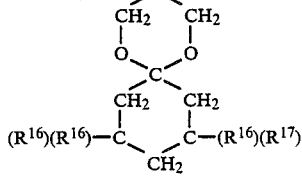 (X)

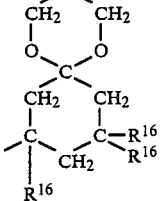 (XI)

2. A compound of claim 1 where in $R^1$ is hydrogen, and X is —O—.

3. A compound of claim 2 which is 1,5-dioxaspiro[5.5]undecane-3,3-diacetic acid, diester with 2,2,6,6,-tetramethylpiperidin-4-ol.

4. A compound of claim 2 which is 1,5-dioxaspiro[5.5]undecane-3,3-diacetic acid, diester with 1,2,2,6,6-pentamethylpiperidin-4-ol.

5. A synthetic polymer composition stabilized against light induced deterioration comprising an organic polymer normally subject to deterioration by light, and from 0.01-5% by weight of a compound of claim 1.

6. A composition of claim 5 wherein the organic polymer is a polyolefin homopolymer or copolymer.

7. A composition of claim 6 wherein said polyolefin is polypropylene.

8. A method of stabilizing organic polymers against light induced deterioration which comprises incorporating therewith from 0.01-5% by weight of a compound of claim 1.

* * * * *